United States Patent [19]

Habermeier et al.

[11] 4,229,576
[45] Oct. 21, 1980

[54] ANTHRANILATES OF OXYALKYLATED CYANURIC ACID

[75] Inventors: Jürgen Habermeier, Pfeffingen; Roland Moser, Basel; Wolfgang Seiz, Pfeffingen, all of Switzerland

[73] Assignee: Ciba-Geigy Corporation, Ardsley, N.Y.

[21] Appl. No.: 966,426

[22] Filed: Dec. 4, 1978

[30] Foreign Application Priority Data

Dec. 9, 1977 [CH] Switzerland .................. 15122/77

[51] Int. Cl.$^2$ ........................................... C07D 251/34
[52] U.S. Cl. ................................................. 544/222
[58] Field of Search ..................................... 544/222

[56] References Cited

U.S. PATENT DOCUMENTS

| 3,123,631 | 3/1964 | Staiger et al. | 260/471 |
| 3,783,150 | 1/1974 | Kolyer et al. | 544/222 |

FOREIGN PATENT DOCUMENTS 847680 10/1975 Belgium .
847681 10/1975 Belgium .
1091949 11/1967 United Kingdom .

OTHER PUBLICATIONS

Cummins, *J. Org. Chem.*, vol. 28, pp. 85–89 (1963).
Dyen et al., *Chemical Reviews*, vol. 67, p. 210 (1967).
Sherwin–Williams Technical Bulletin 152.
Wong et al., *Elastomerics*, p. 37, Mar. 1977.

*Primary Examiner*—John M. Ford
*Attorney, Agent, or Firm*—Joseph F. DiPrima; Harry Falber

[57] ABSTRACT

Novel anthranilates of oxyalkylated cyanuric acid are obtained by reacting the oxyalkylated cyanuric acid, for example 1,3,5-tris-(2'-hydroxyethyl) isocyanurate, with isatoic anhydride. The anthranilates are valuable chain extenders and crosslinking agents in the production of polyurethanes and polyurea resins and can also be used as curing agents for epoxide resins.

5 Claims, No Drawings

ANTHRANILATES OF OXYALKYLATED CYANURIC ACID

The present invention relates to novel anthranilates of oxyalkylated cyanuric acid, processes for their preparation and their use as chain extenders and crosslinking agents in the production of polyurethanes and polyurea resins.

4,4'-Methylene-bis-(o-chloroaniline) (MOCA) has for a long time been one of the best chain extenders and crosslinking agents introduced into polyurethane and polyurea technology, since MOCA, especially in the production of polyurethane elastomers or flexible foams, has advantageous processing characteristics in respect of the reactivity and, moreover, imparts outstanding mechanical properties to the crosslinked polymers. As is known, however, there is a suspicion that MOCA may be carcinogenic (cf. "Elastomerics", March 1977, page 37) and there has been no lack of attempts to replace MOCA by crosslinking agents which are equivalent in respect of the advantageous processing characteristics and the end characteristics of the polymers.

In Technical Bulletin 152 of the "Sherwin-Williams Company" (USA) bis-anthranilates of linear aliphatic diols are mentioned. In "Elastomerics", March 1977, page 37 et seq., 4,4'-methylene-bis-anthranilates are proposed as a replacement for MOCA. Furthermore, in the two Belgian Patent Specifications Nos. 847,680 and 847,681, bis-anthranilates of diols containing a N,N-heterocyclic radical, for example 1,3-di-(2'-hydroxyethyl)-benzimidazoles and 1,3-di-(2'-hydroxyethyl)-5,5-dimethylhydantoin, are disclosed as chain extenders for polyurethanes.

It has now been found that N,N',N''-tris-(hydroxyethyl) isocyanurate surprisingly can be reacted, in the presence of a strong alkali as the catalyst, with isatoic anhydride to give the corresponding anthranilates and that splitting of the isocyanate ring and formation of oxazolidinone compounds virtually cannot be detected. Specifically, it is known that tris-(hydroxyalkyl) isocyanurates very easily rearrange in the presence of alkaline catalysts to give corresponding oxazolidin-2-ones [M. E. Dyen and D. Swern in "Chemical Reviews" 67 (2), page 210 (1967)].

The use of anthranilates of oxyalkylated cyanuric acid as chain extenders and crosslinking agents in urethane and urea formulations also has the advantage that elastomers with better mechanical strength, in particular a higher modulus of elasticity and higher tensile strength, are obtained and these also have better stability to heat.

The present invention thus relates to novel anthranilates of the formula I

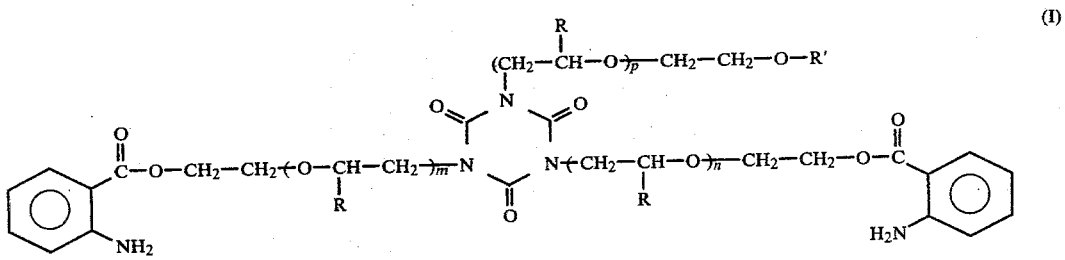

in which the Rs are each a hydrogen atom, methyl or phenyl, R' is a hydrogen atom or anthranoyl and m, n and p are each nought or a number from 1 to 10.

Preferably, in the formula I, the Rs are each a hydrogen atom, R' is a hydrogen atom or anthranoyl and m, n and p are each nought or a number from 1 to 3.

Compounds of particular interest are those of the formula I in which the Rs are each a hydrogen atom, R' is a hydrogen atom or anthranoyl, preferably a hydrogen atom, and m, n and p are each nought.

The compounds of the formula I can be prepared by reacting tris-(hydroxyalkyl) compounds of the formula II

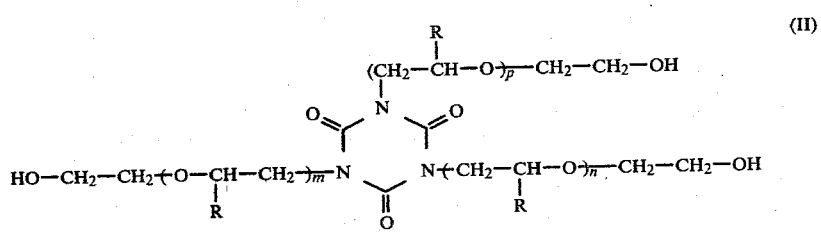

in which R, m, n and p are as defined in formula I, with isatoic anhydride, preferably in the presence of a basic catalyst, to give compounds of the formula I.

The starting materials used in this process are preferably compounds of the formula II in which R is a hydrogen atom and m, n and p are each nought or a number from 1 to 3; in particular, 1,3,5-tris-(2'-hydroxyethyl) isocyanurate is employed as the compound of the formula II.

The compounds of the formula II are known compounds and can be obtained by the process described in J. Org. Chem. 28, (1963), 85–89, by adding the corresponding alkylene oxide onto cyanuric acid. Compounds of the formula II in which R is a hydrogen atom are obtained by adding m+n+p+3 mols of ethylene oxide onto cyanuric acid. When preparing compounds of the formula II in which R is methyl or phenyl, m+n+p mols of propylene oxide or styrene oxide are first added onto cyanuric acid and 3 mols of ethylene oxide are then added on in order to obtain tris-(hydroxyalkyl)-alkyl compounds containing primary hydroxyl groups.

When preparing the compounds, according to the invention, of the formula I, the starting materials are generally employed in approximately stoichiometric amounts. Preferably, however, a slight stoichiometric excess of isatoic anhydride is used, i.e. when preparing diesters of the formula I in which R' is a hydrogen atom, up to 2.2 mols of isatoic anhydride are employed per mol of the tri-(hydroxyalkyl) compound of the formula II and when preparing the triesters of the formula I up to 3.5 mols of isatoic anhydride are used per 1 mol of the tri(hydroxyalkyl) compound of the formula II.

Mixtures of the compounds according to the invention can also be prepared by using the starting materials in molar ratios which are between the molar ratios indicated above. These mixtures are suitable for the same applications as the pure compounds according to the invention, i.e. they can be used both as chain extenders and as crosslinking agents in polyurethanes and polyurea resins.

The preparation of the compounds of the formula I or of mixtures thereof is preferably carried out in the presence of an organic solvent or solvent mixture. Suitable solvents are, in particular, the aprotic solvents, such as dioxan, chloroform, toluene, dimethylformamide and dimethylacetamide.

The reaction temperature for the preparation of the compounds of the formula I or of mixtures thereof can be from 30° to 160° C. Preferably, the reaction is carried out in the temperature range of 50° to 130° C.

Preferably, the conversion reaction is catalysed by bases, and alcoholates, including those of the starting diols, alkali metal hydroxides or alkaline earth metal hydroxides, tertiary amines and ammonium bases or other substances having a basic action can be used. Frequently, basic impurities in the starting materials also suffice. Catalysts can be used in amounts of 0.01 to 10 mol%, based on the amount of isatoic anhydride employed.

The reaction of isatoic anhydride with alcohols, which, as is known, proceeds with the elimination of $CO_2$, is described in detail in U.S. Pat. No. 3,123,631.

Another process for the preparation of the compounds of the formula I comprises esterifying 1 mol of the tris-(hydroxyalkyl) compound of the formula II with 2 or 3 mols of o-nitrobenzoic acid and then reducing the nitro groups in a known manner to the amino groups.

The compounds of the formula I can also be prepared by a transesterification process, by transesterifying the tris-(hydroxyalkyl) compounds of the formula II with anthranilates, preferably alkyl anthranilates having 1 to 4 C atoms in the alkyl group, the alcohol formed during the reaction being distilled off.

The compounds according to the invention are colourless crystalline substances or viscous liquids. Essentially, the values of m, n and p are decisive for the consistency of the novel compounds. If m, n and p are greater than 2, highly viscous liquids form. The higher the value for m, n and p, the lower is the viscosity of the compounds.

The compounds, according to the invention, of the formula I are readily soluble in many organic solvents, such as dioxan, toluene, benzene, dichlorobenzene and dimethylformamide. Furthermore, the novel compounds also have good solubility in higher molecular weight diols, diol-polyether compounds and short-chain polyesters containing hydroxyl groups.

As mentioned initially, the compounds according to the invention are a valuable replacement for 4,4'-methylene-bis-(o-chloroaniline). They can therefore be used in an analogous manner. In particular, the compounds according to the invention are suitable as chain extenders in polyurethanes and as crosslinking agents for the production of polyurea resins. Moreover, they can be used as curing agents for epoxide resins.

EXAMPLE 1

Tris-anthranilate of 1,3,5,-tris-(hydroxyethyl) isocyanurate 44.4 g (0.17 mol) of commercially available 1,3,5-tris-(2'-hydroxyethyl) isocyanurate are stirred in 300 ml of toluene and 60 ml of dimethylformamide in a laboratory reactor fitted with a reflux condenser, a thermometer, a stirrer, external heating and cooling and a feed device for pulverulent material. 0.1 g of sodium hydroxide powder is added, the resulting suspension is warmed to 80° C. and 87.36 g (0.536 mol) of isatoic anhydride are added in 6 portions in the course of 6 hours. A further 0.1 g of sodium hydroxide powder is added 2 hours and 4 hours after the start of the reaction. The reaction proceeds with the evolution of $CO_2$. After the final addition of isatoic anhydride, the reaction mixture is warmed to 90° to 95° C. and stirred for a further 4.5 hours under these conditions. It is cooled to 20° C. and filtered and the clear, pale yellow filtrate is concentrated to dryness. The residue is then dried to constant weight under 0.8 mm Hg at 110° C. This yields 106 g of a pale brown residue which crystallises slowly. The crude product is recrystallised from 700 ml of acetone and is then recrystallised a second time from dioxan/ethanol, 1:1. This yields 73.1 g of a colourless, crystalline product which melts at 186° to 188° C. Elementary analysis gives, for $C_{30}H_{30}N_6O_9$: Found: C, 58.15%; H, 4.90%; N, 13.25%. Calculated: C, 58.25%; H, 4.89%; N, 13.59%.

The H-NMR spectrum is in accord with the structure given below.

The thin layer chromatogram (TLC) confirms the purity of the product. Traces of the diester (R'=H) can be detected as a by-product by means of TLC.

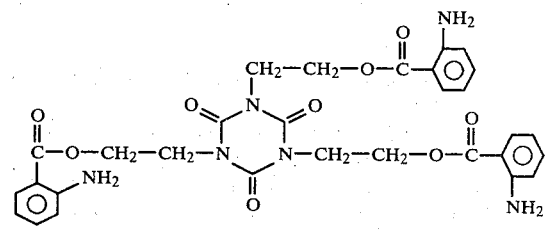

EXAMPLE 2

Tris-anthranilate of polyoxyethylated cyanuric acid (a) Preparation of the starting material 78.3 g (0.3 mol) of pure tris-(hydroxyethyl) isocyanurate recrystallised from methanol are dissolved in 750 ml of dioxan at 60° C. and 1.5 ml of boron trifluoride diethyl etherate solution (in diethyl ether, 47% solution) are added. 23.6 g (1.05 mols) of ethylene oxide are passed in as a gas in the course of 2½ hours, with gentle stirring. The reaction is exothermic; the heating bath is removed and the resulting temperature is 60 to 67° C. After all of the ethylene oxide has been introduced, the reaction mixture is stirred for a further 1 hour at 60° C. and is then cooled to 20° C., 1.5 ml of 50% sodium hydroxide solution are added and the resulting mixture is concentrated completely. After drying the residue to constant weight at 110° C./10.25 mm Hg, 124 g of the clear, pale brown, liquid product are obtained. The combustion analyses are in accord with the structure given below. On the basis of gas chromatograms (GC) after silylation by means of conventional silylating reagents, the following distribution of oligomers exists (GC temperature: 290° C; column SP 2100; carrier gas: He).

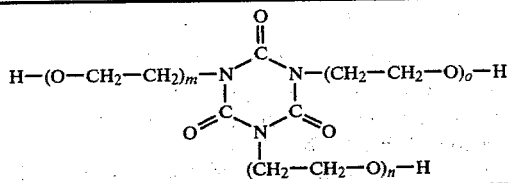

| | |
|---|---|
| m + n + o = 3:24 mol% | m + n + o = 7:13 mol% |
| m + n + o = 4:21 mol% | m + n + o = 8:7 mol% |
| m + n + o = 5:17 mol% | m + n + o = 9:3 mol% |
| m + n + o = 6:15 mol% | |

(b) Preparation of the tris-anthranilate 120.9 g of the triol obtained under 2(a) are heated with 60 ml of dioxane to 60° C. 0.1 g of KOH powder (85% pure) is then added and 43.5 g of isatoic anhydride are added. The yellow suspension is stirred at 60° C. and a slight evolution of $CO_2$ is discernible. After 40 minutes, a further 0.1 g of KOH powder (85% pure) and 43.5 g of isatoic anhydride are added and immediately thereafter the reaction mixture is heated to 80° C. The vigorous evolution of $CO_2$ which starts has subsided after about 60 minutes and a turbid yellow-brown reaction mixture forms. After a total of 100 minutes at 80° C., a further 0.1 g of KOH powder and 43.5 of isatoic anhydride are added. The evolution of $CO_2$ is again visible and this subsides after about 30 minutes. The reaction is allowed to continue for a further 2 hours at 80° C. and the reaction mixture is then heated to 100° C. After 5 hours at 100° C., the reaction solution is completely concentrated. 150 ml of chloroform are added to the residue and the mixture is extracted as follows: twice with 100 ml of ammonia solution (10%), twice with 200 ml of deionised water, twice with 100 ml of ammonia solution (10%) and 4 times with 100 ml of deionised water.

After clarifying over active charcoal and "Hyflo", the chloroform phase is totally evaporated under a water pump vacuum at 80° C. After drying the residue to constant weight at 120° C./0.2 mm Hg, 98.8 g of a brownish, tacky resin are obtained. The combustion analyses confirm the structure given below.

EXAMPLE 3

Tris-anthranilate of 1,3,5-tris-(2'-hydroxy-n-propyl) isocyanurate

In the apparatus described in Example 1, 283.3 g (0.934 mol) of 1,3,5-tris-(2'-hydroxypropyl) isocyanurate are stirred with 1,120 ml of toluene and 470 ml of dimethylformamide at 80° C. After adding 0.87 g of potassium hydroxide powder, 167.5 g (1.03 mols) of isatoic anhydride are added. After the evolution of $CO_2$ has subsided, the same amounts of potassium hydroxide and isatoic anhydride are again added. A third addition of KOH and isatoic anhydride (the same amounts) is made 1½ hours later. The reaction mixture is then heated to 100° C. and kept at this temperature for 4 hours, a further 50 ml of dimethylformamide being added. After cooling to room temperature, the brown solution is freed from a small amount of precipitate by filtering and the filtrate is concentrated. The residue is then dried at 120° C. and about 0.8 mm Hg. The resulting brittle resin weighs 555.7 g. According to the thin layer chromatogram, the crude product also contains, in addition to the main product, 2 by-products in small amounts.

EXAMPLE 4

Tris-anthranilate of 1,3,5-tris-(2'-hydroxy-2'-phenylethyl) isocyanurate

In the apparatus described in Example 1, 425 g (0.868 mol) of 1,3,5-tris-(2'-hydroxy-2'-phenylethyl) isocyanurate are stirred with 1,040 ml of toluene and 437 ml of dimethylformamide at 80° C., 0.81 g of potassium hydroxide powder and 155.7 g (0.92 mol) of isatoic anhydride are added and the mixture is kept at 80° C. for 1 hour. A further addition of 0.81 g of KOH and 155.7 g of isatoic anhydride is then made. Exactly the same procedure is followed a 3rd time 1½ hours later. The reaction mixture is then heated to 100° C. and a further 100 ml of dimethylformamide are added. The dark brown reaction mixture is kept at 100° C. for a further 4 hours and is then cooled to room temperature. The brown solution obtained after filtering is then evaporated to dryness. After drying the residue to constant weight at 120° C. and about 0.8 mm Hg, 633.3 g of a brittle brown resin are obtained. The thin layer chromatogram shows that the crude product also contains impurities, in addition to the main product.

APPLICATION EXAMPLES

EXAMPLE A

A prepolymer is prepared from 50 g of a low molecular weight polyester of adipic acid and ethylene glycol,

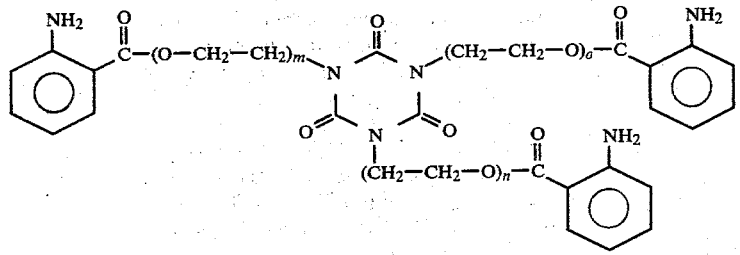

in which m, n and o correspond to the values for Example 2(a).

which has hydroxyl end groups and a OH number of 55 (available commercially under the name "Desmophen 2000") and which has previously been freed from traces of water by heating (for 3 hours at 130° C.) in vacuo (0.5 mm Hg), and 25.0 g of 4,4'-diisocyanato-diphenylmethane (available commercially under the name "Desmodur 44 V"), by stirring for 30 minutes at 110° C.

A mixed melt of 30 g of "Desmophen 2000" and 9.9 g of the tris-anthranilate prepared according to Example 1 (dissolved at 130° C. to give a clear solution and then cooled to about 100° C.) is stirred into this prepolymer, which is still at about 100° C. This casting resin mixture is poured into aluminium moulds with a wall thickness of 4 mm and is cured completely at 140° C. in the course of 5 hours.

The elastomeric moulding thus obtained has excellent mechanical properties.

EXAMPLE B

In the manner described in Example A, a prepolymer is prepared from 70 g of the polyester used in Example A and 34 g of toluylene diisocyanate (available commercially under the name "Desmodur T 100").

This prepolymer is mixed at 90° to 100° C. with a homogeneous solution of 40 g of "Desmophen 2000" and 9.9 g of the tris-anthranilate prepared according to Example 1.

After curing according to Example A, transparent, pale yellow, elastomeric mouldings are obtained.

EXAMPLES C and D

A liquid prepolymer which has been prepared from toluylene diisocyanate and polytetramethylene glycol and has an isocyanate content of 1.5 equivalents/kg and a viscosity of about 10,000 mPa.s at 25° C. (available commercially under the name "Adipren L-167") was mixed in equivalent amounts with the tris-anthranilates prepared in Examples 1 and 2. The mixtures obtained after intimate mixing were freed in vacuo from the air stirred in and then poured into aluminium moulds, pretreated with mould-release agents, to produce sheets with dimensions of 135×135×4 mm and 135×135×1 mm and crosslinked, for 4 hours at 140° C. in the case of Example C and for 6 hours at 120° C. in the case of Example D.

Test pieces which correspond to DIN (DIN=Deutsche Industrienorm) (German Industrial Standard)) 53,455, No. 4 were stamped out from the 4 mm thick sheets using a punch and the tests to determine the tensile strength and elongation at break were carried out on these. The remainder of the 4 mm sheet was used for determining the Shore A hardness (DIN 53,505) and the impact resilience according to DIN 53,455.

Shaped pieces for determining the tear propagation resistance according to DIN 53,363 were cut out from the 1 mm thick sheet.

The results obtained are listed in Table 1.

TABLE 1

| Example | C | D |
|---|---|---|
| Tris-anthranilate | according to Example 1 | according to Example 2 |
| Parts by weight of anthranilate per 100 parts by weight of prepolymer | 27.8 | 38.7 |
| Processing conditions | prepolymer warmed to 120° C. and anthranilate warmed to 180° C. | prepolymer and anthranilate warmed to 80° C. |
| Appearance of the elastomers | pale brown, transparent | yellow, slightly opaque |
| Shore A hardness (units) | 84 | 69 |
| Tensile strength (N/mm$^2$) | 23 | 13.3 |
| Elongation at break (%) | 307 | 348 |
| Tear propagation resistance (N/mm) | 150 | 27 |
| Impact resilience (%) | 21 | 10 |

EXAMPLES E and F

The constituents of these mixtures were in each case mixed in the ratios and under the processing conditions indicated in Table 2. The resin component was again the isocyanate prepolymer used in Examples C and D ("Adipren L-167"). In order to obtain flawless castings, the air stirred in was removed from the prepolymer/anthranilate mixture by means of vacuum and only then was the mixture poured into aluminium moulds, pretreated with mould-release agents, to produce 4 mm thick test sheets. Crosslinking to obtain the elastomer was carried out for 6 hours at 120°. The tests to determine the Shore A hardness (DIN 53,505) and the impact resilience (DIN 53,455) were carried out on the sheets of moulded material thus obtained. The results obtained are listed in Table 2.

TABLE 2

| Example | E | F |
|---|---|---|
| Tris-anthranilate | according to Example 3 | according to Example 4 |
| Parts by weight of anthranilate per 100 parts by weight of prepolymer | 26.4 | 33.8 |
| Processing conditions | prepolymer warmed to 80° C. and the molten anthranilate, warmed to 100° C., mixed in | |
| Appearance of the elastomers | brown, transparent | brown, transparent |
| Shore A hardness (units) | 66 | 70 |
| Impact resilience (%) | 9 | 9 |

EXAMPLE G to I

A liquid, unmodified epoxide resin based on bisphenol A with an epoxide content of 5.4 equivalents/kg and a viscosity of about 10,000 mPa.s/25° C. was mixed in equivalent ratios with the tris-anthranilates prepared in Examples 1, 3 and 5 and the mixtures were melted together and cured under the conditions indicated in Table 3.

4 g amounts of the mixtures thus obtained were poured into small aluminium dishes about 5 cm in diameter. The glass transition temperature of the moulded material obtained after curing was then determined using a Thermoanalyzer (type TA 2000 from Mettler, Griefensee, Switzerland).

A further portion of resin/curing agent mixture was applied to a glass plate and cured in an oven in accordance with the data in Table 3. The chemical resistance of the film thus obtained was determined, the procedure being as follows:

The appearance of the film was described briefly (visual). One drop of each of the particular chemicals was then left on the film for 1 hour. After this period of action, the chemicals were wiped off and the surface of the film graded visually, grade 1 being given for no visible attack, grade 2 for slight attack and grade 3 for severe attack on the surface of the film and grade 4 being given for complete destruction of the film.

TABLE 3

Processing and end characteristics of the casting resin mixtures

| Example | G | H | I |
|---|---|---|---|
| Tris-anthranilate (curing agent) | according to Example 1 | according to Example 3 | according to Example 5 |
| Parts of curing agent per 100 parts of epoxide resin | 55.6 | 59.4 | 76.1 |
| Processing conditions | resin and curing agent mixed at 180° C. | resin and curing agent mixed at 100° C. | resin and curing agent mixed at 100° C. |
| Curing conditions (hours/°C.) | 8/140 and 6/180 | 8/140 and 6/180 | 8/140 and 6/180 |
| Appearance of the moulded material | brown | brown | brown |
| Glass transition temperature (°C.) | 94 | 77 | 82 |
| Appearance of the lacquer film | pale brown, high gloss | pale brown, high gloss | brown, high gloss |
| Chemical stability towards 5N H$_2$SO$_4$ | 1 | 1 | 1 |
| 5N NaOH | 1 | 1 | 1 |
| H$_2$O | 1 | 1 | 2 |
| Cl-benzene | 1 | 2 | 2 |

What is claimed is:

1. An anthranilate of the formula I

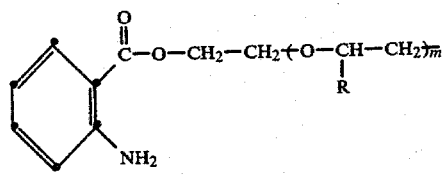

(I)

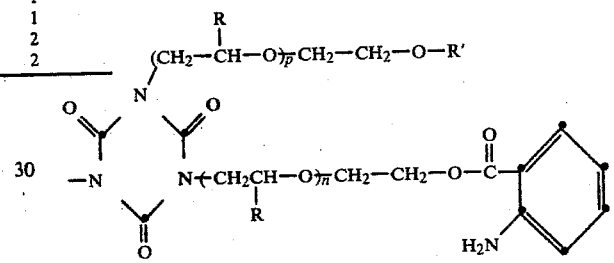

in which each R is hydrogen, methyl or phenyl R' is a hydrogen or anthranoyl and m, n and p are each nought or a number from 1 to 10.

2. An ester according to claim 1, in which, in the formula I, each R is hydrogen, R' is a hydrogen or anthranoyl and m, n and p are each nought or a number from 1 to 3.

3. A compound as claimed in claim 1, which is 1,3,5-Tris-(anthranoyloxyethyl)-isocyanurate.

4. A compound as claimed in claim 1, which is 1,3,5-Tris-(2'-anthranoyloxy-n-propyl)-isocyanurate.

5. A compound as claimed in claim 1, which is 1,3,5-Tris-(2'-anthranoyloxy-2'-phenylethyl)-isocyanurate.

* * * * *